The concentrates containing the viscosity regulators were heated on a steam bath until clear liquids were obtained. After the liquids had been defoamed in a centrifuge, their viscosities were determined at various temperatures in a Hoppler falling-ball viscosimeter. The reduction in viscosity obtained is shown in the following Table I.

TABLE I

| Ex. No. | Viscosity Regulator & % by wt. | pH Value | Surfactant Concentration % by wt. | Viscosity mPas at 70° C. |
| --- | --- | --- | --- | --- |
| 1 | A 10 | 4 | 51 | 900 |
| 2 | A 10 | 7 | 49 | 1100 |
| 3 | B 10 | 4 | 53 | 590 |
| 4 | B 10 | 7 | 53 | 960 |
| 5 | A 5 + B 5 | 4 | 60 | 530 |
| 6 | C 10 | 5 | 52 | 575 |

By contrast, an α-sulfotallow fatty acid methyl ester concentrate containing approximately 50% by weight of active substance showed a viscosity of more than 50,000 mPas at 65° C. in the absence of a viscosity regulator while an approximately 29% by weight concentrate showed a viscosity of approximately 25,000 mPas.

When viscosity regulators A, B and C were replaced by others of the above-mentioned compounds, i.e. α-sulfosuccinic acid ethyl ester, α-sulfoadipic acid methyl ester and α-chlorovaleric acid, comparable effects were obtained. Concentrates of tallow alcohol sulfates give similar results. An increase in the working temperature also has a viscosity-reducing effect, although this will accordingly require a greater consumption of energy.

The preceding specific embodiments are illustrative of the practice of the invention. It is to be understood, however, that other expedients known to those skilled in the art or disclosed herein may be employed without departing from the spirit of the invention or the scope of the appended claims.

What is claimed is:

1. An aqueous concentrate of an anionic surfactant having a viscosity at 70° C. of not more than about 10,000 mPas comprising:
   A. an α-sulfo fatty acid ester; and
   B. a viscosity reducing amount of a salt of at least one of the following viscosity regulators: α-sulfoadipic acid methyl ester, α-chlorovaleric acid, cyanoacetic acid, and cyanoacetic acid ethyl ester;

and wherein component A. is present in an excess of 30% by weight, based on the weight of the concentrate.

2. A concentrate in accordance with claim 1 wherein said salt in component B. is the sodium salt.

3. A concentrate in accordance with claim 1 wherein said concentrate has a pH below 7.

4. A concentrate in accordance with claim 1 wherein said viscosity regulator B. is employed in an amount of from about 1 to about 15% by weight based on the weight of component A.

5. A concentrate in accordance with claim 1 wherein said viscosity regulator B. is employed in an amount of from about 7 to about 12% by weight, based on the weight of component A.

6. A method for the manufacture of powdery or granular spray dried detergents and cleaners comprising the steps of:
   I. forming an aqueous anionic surfactant concentrate having a viscosity at 70° C. of not more than about 10,000 mPas comprising
      A. an α-sulfo fatty acid ester; and
      B. a viscosity reducing amount of a salt of at least one of the following viscosity regulators: α-sulfoadipic acid methyl ester, α-chlorovaleric acid, cyanoacetic acid, and cyanoacetic acid ethyl ester;
   and wherein component A. is present in an excess of 30% by weight, based on the weight of the concentrate; and
   II. spray drying the concentrate at a temperature in the range of from about 60° to about 90° C.

7. A method in accordance with claim 6 wherein other detergent ingredients are added to the concentrate prior to spray drying.

8. A method in accordance with claim 6 wherein said salt in component B. is the sodium salt.

9. A method in accordance with claim 6 wherein said concentrate in step I has a pH below 7.

10. A method in accordance with claim 6 wherein the viscosity regulator in step I. B. is employed in an amount of from about 1 to about 15% by weight, based on the weight of component A.

11. A method in accordance with claim 6 wherein the viscosity regulator in step I. B. is employed in an amount of from about 7 to about 12% by weight, based on the weight of component A.

* * * * *

United States Patent

Torii et al.

[11] Patent Number: 4,532,077
[45] Date of Patent: Jul. 30, 1985

[54] THIAZOLINEAZETIDINONE-TYPE COMPOUNDS

[75] Inventors: Sigeru Torii; Kenji Uneyama; Hideo Tanaka; Junzo Nokami; Takashi Shiroi, all of Okayama; Norio Saito, Tokushima, all of Japan

[73] Assignee: Otsuka Kagaku Yakuhin Kabushiki Kaisha, Japan

[21] Appl. No.: 411,391

[22] Filed: Aug. 25, 1982

[51] Int. Cl.³ .............................................. C07D 513/04
[52] U.S. Cl. ..................................... 260/245.4; 204/81
[58] Field of Search ......................................... 260/245.4

[56] References Cited

U.S. PATENT DOCUMENTS

| | | | |
|---|---|---|---|
| 4,058,521 | 11/1977 | Uyeo et al. | 260/239.1 |
| 4,183,855 | 1/1980 | Yoshioka | 260/245 X |
| 4,271,296 | 6/1981 | Tsuji | 260/245.4 |

FOREIGN PATENT DOCUMENTS

| | | | |
|---|---|---|---|
| 7059896 | 4/1982 | Japan | 260/245.4 |
| 7059897 | 4/1982 | Japan | 260/245.4 |
| 1410371 | 10/1975 | United Kingdom. | |

OTHER PUBLICATIONS

Fieser & Fieser, Reagents for Chem. Synthesis, 1967, p. 1278.

Andrews et al., Tetrahedron Letters, 693–696, (1980).
Crossland et al., J. Organic Chem. 35, 3195-6.
Shono et al., Tetrahedron Letters 2157–2160, (1979).

*Primary Examiner*—Mark L. Berch
*Attorney, Agent, or Firm*—Larson and Taylor

[57] ABSTRACT

This invention relates to novel thiazolineazetidinone-type compounds represented by the formula

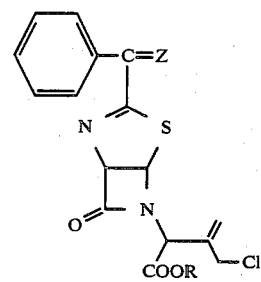

wherein R represents a hydrogen atom, alkyl group, alkyl group replaced with halogen atoms, methyl group replaced with substituted or unsubstituted phenyl groups, methyl replaced with halogen atoms, or trialkylsilyl group and Z represents O or $Cl_2$.

2 Claims, No Drawings

THIAZOLINEAZETIDINONE-TYPE COMPOUNDS

This invention relates to thiazolineazetidinone-type compounds and particularly to thiazolineazetidinone-type compounds represented by the formula

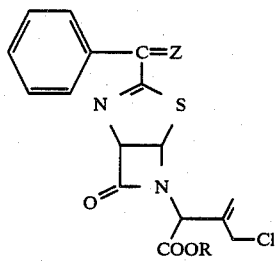

wherein R represents an alkyl group, alkyl group replaced with halogen atoms, methyl group replaced with substituted or unsubstituted phenyl groups, methyl group replaced with halogen atoms or trialkylsilyl group and Z represents O or $Cl_2$.

The compounds of this invention are useful as the intermediates for synthesizing β-lactam-type antibiotics.

Examples of the alkyl groups represented by R in the formula (1) are methyl, ethyl, butyl, hexyl and like lower alkyl groups, etc. Examples of the halogen atoms are chlorine, bromine, iodine, etc. Examples of the substituted phenyl groups are those substituted with alkyl, alkoxy, halogen, nitro and the like, etc. Examples of the alkyl and alkoxy groups as the foregoing substituents are lower alkyl groups and lower alkoxy groups, such as methyl, ethyl, butyl, propyl, hexyl, methoxy, butoxy, propoxy, etc. Examples of the trialkylsilyl groups are trimethylsilyl, triethylsilyl, dimethylmonobutylsilyl, monomethyldibutylsilyl, etc.

The compounds of the formula (1) can be prepared for example by electrolyzing a compound represented by the formula

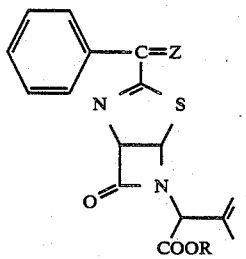

wherein R and Z are as defined above in a homogeneous or inhomogeneous solvent comprising water and an organic solvent in the presence of a halide and/or hydrohalogenic acid.

The compounds of the formula (2) to be used as the starting material in the foregoing process are those heretofore known and can be easily prepared for example by the process disclosed in J.A.C.S. 92 2575 (1970).

Organic solvents useful in the electrolysis of this invention include methyl acetate, ethyl acetate, butyl acetate, methyl formate, ethyl formate, ethyl propionate and like esters of carboxylic acids, diethyl ether, dibutyl ether, tetrahydrofuran, dioxane, ethylene glycol dimethyl ether and like ethers, dichloromethane, chloroform, carbon tetrachloride, dibromoethane and like hydrocarbon halides, acetonitrile, butyronitrile and like nitriles, methanol, ethanol, isopropanol, butanol, tertiary-butanol and like alcohols, pentane, hexane, cyclohexane and like hydrocarbons, benzene, toluene, xylene, chlorobenzene, and like aromatic compounds, etc. These organic solvents are used singly or in mixture.

In the electrolysis of this invention, the organic solvents are employed as a rule in mixture with water. The proportions of the former to the latter are 1:100 to 100:1 preferably 1:20 to 2:1. The mixed solvent may be in homogeneous or inhomogeneous form.

Exemplary of useful halides to be used as a supporting electrolyte are sodium chloride, potassium chloride, lithium chloride and like alkali metal salts, magnesium chloride, barium chloride, calcium chloride and like alkaline earth metal salts, ammonium chloride, tetramethylammonium chloride, tetraethylammonium chloride, tetrabutylammonium chloride, and like chlorinated ammonium and quaternary ammonium salts. Also usable as such halides are bromides, fluorides and iodides thereof.

Hydrochloric acid is employable as the hydrohalogenic acid. In the hydrohalogenic acid and/or halide can be incorporated a mineral acid other than the hydrohalogenic acid, an organic acid. Typical examples of mineral acids are, for example, sulfuric acid, nitric acid, carbonic acid, potassium hydrogensulfate, sodium hydrogensulfate, phosphoric acid, etc. Useful organic acids include mono-carboxylic acid or dicarboxylic acid having 1 to 15 carbon atoms, organic sulfonic acid having 1 to 10 carbon atoms, etc. Specific examples of these acids are formic acid, acetic acid, propionic acid, butyric acid, tartaric acid, oxalic acid, citric acid, phthalic acid, malic acid, paratoluenesulfonic acid, etc.

The electrolysis of this invention can be carried out at a current density in the range of usually about 5 to about 500 $mA/cm^2$, preferably about 10 to about 50 $mA/cm^2$. Electrode materials are those usually used such as platinum, carbon, stainless steel, lead oxide and nickel. The electrolysis is conducted at a temperature between about $-20°$ to about 100° C., preferably about $-10°$ to about 50° C. The electrolytic reaction is feasible with or without a diaphragm.

The required electric charge is usually about 2 to about 50 F/mol, although variable depending on the shape of the electrolytic cell, the kind of electrodes, the concentration of the substrate, the reactivity of the substrate, etc. The application of current at the electric charge in this range gives contemplated compounds of the formula (1) with extremely high purity in a yield as high as 85 to 95%.

When electrolyzing a compound of the formula (2) wherein R is a methyl group replaced with substituted or unsubstituted phenyl groups, the hydrogen atom constituting the methyl group may be halogenated. Stated more specifically, when R is $-CH(C_6H_5)_2$ as in Example 5 to be described later, the group is converted to $-CCl(C_6H_5)_2$ in the electrolysis of this invention. The compounds of the invention include those thus obtained.

The compounds of the formula (1) are useful as intermediates for synthesizing β-lactam type antibiotics and can be prepared by a process given below.

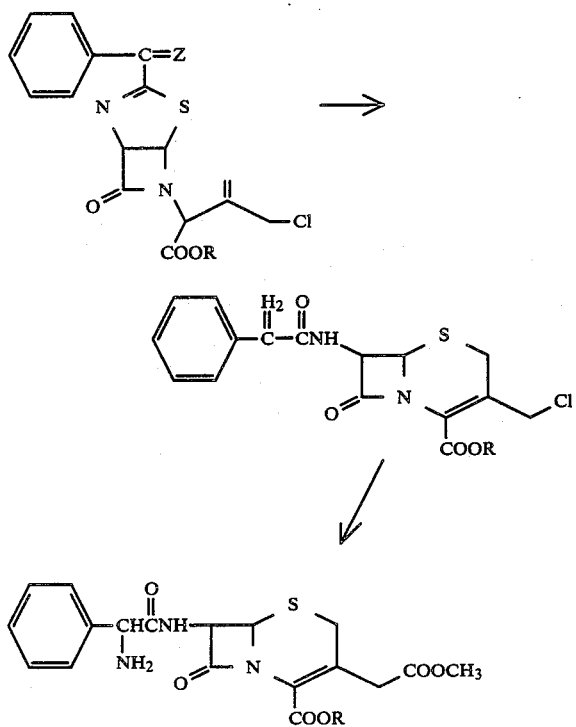

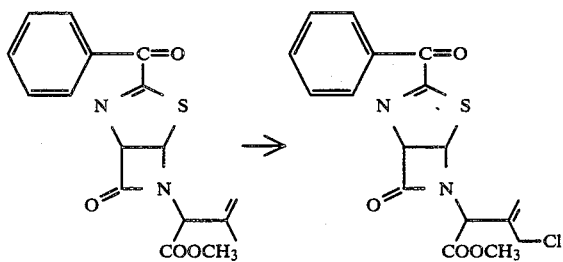

This invention will be described below in detail with reference to examples.

EXAMPLE 1

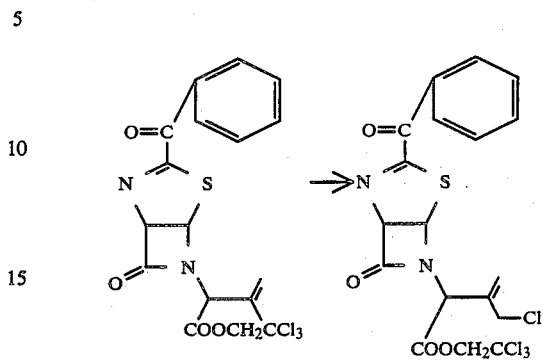

Into a reactor were placed 50 mg of methyl ester of 2-(3-benzoyl-7-oxo-4-thio-2,6-diazabicyclo[3,2,0]hept-2-en-6-yl)-3-methyl-3-butenoic acid serving as the starting material, 0.07 ml of con. sulfuric acid, 5 ml of methylene chloride and a solution of 1 g of sodium chloride in 3 ml of water. Electrolysis was conducted at 25° C. and 1.6 to 1.8 V by using platinum electrodes while applying current in an amount of 30 mA. Thereafter the reaction mixture was extracted with 30 ml of methylene chloride. The extract was washed successively with an aqueous solution of sodium sulfite, with an aqueous solution of sodium hydrogencarbonate and then with an aqueous solution of sodium chloride and subsequently was dried over anhydrous sodium sulfate. Then the solvent was removed, and 74 mg of a light yellow liquid was obtained. The liquid was subjected to silica gel column chromatography using an ethyl acetate-benzene mixture as the developer, producing 51 mg of contemplated compound in a yield of 93%.

IR 1780, 1745, 1660, 1600, 858 cm$^{-1}$

NMR(CDCl$_3$) 3.97 (3H, s, COOCH$_3$), 4.16 (2H, s, —CH$_2$Cl), 5.23 (2H, d, J=4 Hz, C=CH$_2$), 5.55 (1H, s, CH—COOCH$_3$), 5.96 (1H, d, J=4 Hz, —CH), 6.37 (1H, d, J=4 Hz, —CH), 7.4–8.4 (5H, m, phenyl)

EXAMPLE 2

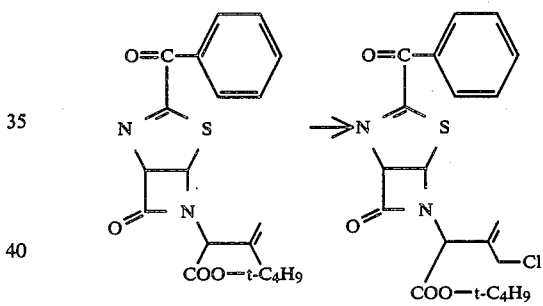

The reaction schematically illustrated above was carried out by using 50 mg of the starting material in a manner similar to that of Example 1, giving 50.5 mg of contemplated compound in a 93.5% yield.

NMR(CDCl$_3$) 4.89 (2H, s, —CH$_2$CCl$_3$), 4.16 (2H, s, —CH$_2$Cl), 5.23 (2H, d, C=CH$_2$), 5.55 (1H, s, CH—COOCH$_2$CCl$_3$)

EXAMPLE 3

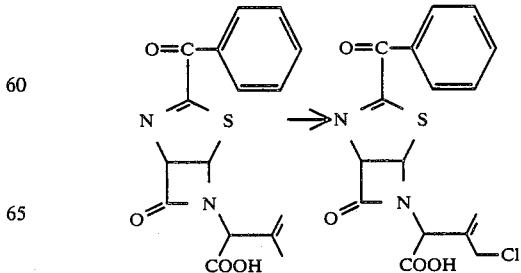

Into a reactor were placed a solution of 1 g of sodium chloride in 3 ml of water, 50 mg of the starting compound, 0.07 ml of con. sulfuric acid and 5 ml of methylene chloride. A procedure similar to that of Example 1 was conducted, giving 51.8 mg of contemplated compound. Yield 95%.

NMR(CDCl$_3$) 1.38 (9H, s, COO—t—C$_4$H$_9$), 3.81 (2H, s, CH$_2$Cl), 5.14 (2H, s, C=CH$_2$), 5.41 (1H, s, CHCOO—t—C$_4$H$_9$), 7.3–7.9 (5H, m, phenyl)

EXAMPLE 4